United States Patent
Pazenok et al.

(10) Patent No.: US 9,914,704 B2
(45) Date of Patent: Mar. 13, 2018

(54) PROCESS FOR PREPARING 3,5-BIS(HALOALKYL)PYRAZOLES VIA ACYLATION OF KETIMINES

(71) Applicant: Bayer CropScience Aktiengesellschaft, Monheim am Rhein (DE)

(72) Inventors: Sergii Pazenok, Solingen (DE); Norbert Lui, Odenthal (DE)

(73) Assignee: Bayer CropScience Aktiengesellschaft, Monheim am Rhein (DE)

( * ) Notice: Subject to any disclaimer, the term of this patent is extended or adjusted under 35 U.S.C. 154(b) by 0 days.

(21) Appl. No.: 15/317,927

(22) PCT Filed: Jun. 8, 2015

(86) PCT No.: PCT/EP2015/062685
§ 371 (c)(1),
(2) Date: Dec. 9, 2016

(87) PCT Pub. No.: WO2015/189138
PCT Pub. Date: Dec. 17, 2015

(65) Prior Publication Data
US 2017/0114020 A1  Apr. 27, 2017

(30) Foreign Application Priority Data
Jun. 11, 2014  (EP) .................................. 14172036

(51) Int. Cl.
*C07D 231/12* (2006.01)
*A01N 43/56* (2006.01)

(52) U.S. Cl.
CPC .......... *C07D 231/12* (2013.01); *A01N 43/56* (2013.01)

(58) Field of Classification Search
None
See application file for complete search history.

(56) References Cited

U.S. PATENT DOCUMENTS 9,309,202 B2 * 4/2016 Pazenok .............. C07C 229/30
9,617,220 B2 * 4/2017 Pazenok .............. C07D 231/16

FOREIGN PATENT DOCUMENTS

| WO | WO-2003070705 | 8/2003 |
|---|---|---|
| WO | WO-2008013925 | 1/2008 |
| WO | WO-2008022777 | 2/2008 |
| WO | WO-2005042468 | 5/2008 |
| WO | WO-2009106230 | 9/2009 |
| WO | WO-2009112157 | 9/2009 |
| WO | WO-2012025557 | 3/2012 |
| WO | WO-2013113829 | 8/2013 |
| WO | WO-2014033164 | 6/2014 |

OTHER PUBLICATIONS

Extended European Search Report dated Aug. 28, 2014 for European Application No. 14172036.7 filed on Jun. 11, 2014, 5 pages.
International Search Report dated Jul. 16, 2015 for PCT Application No. PCT/EP2015/062685 filed on Jun. 8, 2015, 10 pages.
Pashkevich et al. (1981). "Fluoroalkyl containing mono- and bispyrazoles", *Zhurnal Vsesoyuznogo Khimicheskogo Obshchestva im. D. I. Mendeleeva* 26(1):105-107, XP009179740. (English translation included).

\* cited by examiner

*Primary Examiner* — Kamal Saeed
(74) *Attorney, Agent, or Firm* — Morrison & Foerster LLP

(57) ABSTRACT

The present invention relates to a novel process for preparing 3,5-bis(haloalkyl)pyrazole derivatives of the formula (Ia) and (Ib), via acylation of ketimines.

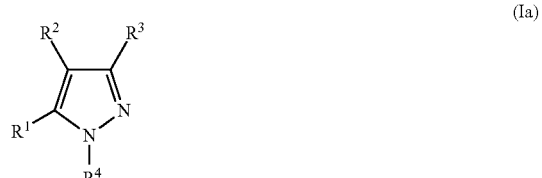

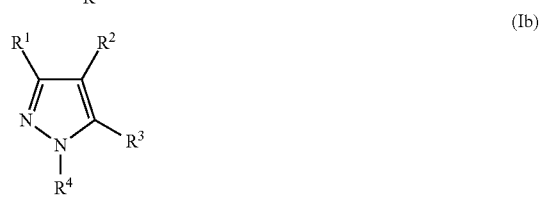

5 Claims, No Drawings

PROCESS FOR PREPARING 3,5-BIS(HALOALKYL)PYRAZOLES VIA ACYLATION OF KETIMINES

CROSS REFERENCE TO RELATED APPLICATIONS

This application is the national stage of International Application No. PCT/EP2015/062685, filed internationally on Jun. 8, 2015, which claims the benefit of European Application No. 14172036.7, filed Jun. 11, 2014, the disclosures of which are hereby incorporated by reference in their entireties for all purposes.

The present invention relates to a novel process for preparing 3,5-bis(haloalkyl)pyrazole derivatives.

Polyfluoroalkylpyrazolylcarboxylic acid derivatives and 3,5-bis(haloalkyl)pyrazoles are valuable precursors of active fungicidal ingredients (WO 2003/070705, WO 2008/013925, WO 2012/025557).

Pyrazolecarboxylic acid derivatives are typically prepared by reacting acrylic acid derivatives having two leaving groups with hydrazines (WO 2009/112157 and WO 2009/106230). WO 2005/042468 discloses a process for preparing 2-dihaloacyl-3-aminoacrylic esters by reacting acid halides with dialkylaminoacrylic esters and subsequent cyclization thereof with alkyl hydrazines. WO 2008/022777 describes a process for preparing 3-dihalomethylpyrazole-4-carboxylic acid derivatives by reacting α,α-difluoroamines in the presence of Lewis acids with acrylic acid derivatives and subsequent reaction thereof with alkylhydrazines.

3,5-Bis(fluoroalkyl)pyrazoles are prepared by reacting bisperfluoroalkyl diketones (e.g. 1,1,1,5,5,5-hexafluoroacetylacetone) with hydrazines (cf. Pashkevich et al., Zhurnal Vsesoyuznogo Khimicheskogo Obshchestva im. D. I. Mendeleeva (1981), 26(1), 105-7), the yield being only 27-40%. The synthesis, isolation and purification of the polyfluoroalkyl diketones is very complex since the compounds are generally very volatile and highly toxic.

In the light of the prior art described above, it is an object of the present invention to provide a process that does not have the aforementioned disadvantages and hence gives a route to 3,5-bis(haloalkyl)pyrazole derivatives in high yields.

The object described above was achieved by a process for preparing 3,5-bis(haloalkyl)pyrazoles of the formula (Ia) and (Ib),

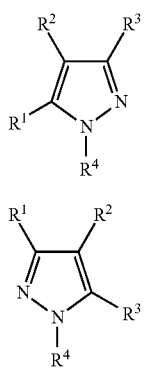

in which
$R^1$ and $R^3$ are each independently selected from $C_1$-$C_6$-haloalkyl;
$R^2$ is selected from H, halogen, COOH, (C=O)OR$^5$, CN and (C=O)NR$^6$R$^7$;
$R^4$ is selected from H, $C_1$-$C_8$ alkyl, aryl, pyridyl;
$R^5$ is selected from $C_{1-12}$-alkyl, $C_{3-8}$-cycloalkyl, $C_{6-18}$-aryl, $C_{7-19}$-arylalkyl and $C_{7-19}$-alkylaryl;
$R^6$ and $R^7$ are each independently selected from $C_{1-12}$-alkyl, $C_{3-8}$-cycloalkyl, $C_{6-18}$-aryl, $C_{7-19}$-arylalkyl and $C_{7-19}$-alkylaryl, or where
$R^6$ and $R^7$ together with the nitrogen atom to which they are bonded may form a four-, five- or six-membered ring
characterized in that in step (A), acid derivatives of the formula (II),

in which
$R^1$ is as defined above;
X is F, Cl, Br or —OC(O)R$^1$
are reacted with compounds of the formula (III),

in which
$R^8$ is selected from $C_{1-12}$-alkyl, $C_{3-8}$-cycloalkyl, $C_{6-18}$-aryl, $C_{7-19}$-arylalkyl and $C_{7-19}$-alkylaryl, OR$^9$;
$R^9$ is selected from $C_{1-12}$-alkyl, $C_{3-8}$-cycloalkyl, $C_{6-18}$-aryl, $C_{7-19}$-arylalkyl, $C_{7-19}$-alkylaryl;
$R^2$ and $R^3$ are as defined above;
to form the compounds of formula (IV)

in which
$R^1$, $R^2$, $R^3$, $R^5$, $R^6$, $R^7$, $R^8$, $R^9$ are as defined above
and that in step (B) cyclization of (IV) in the presence of (V) NH$_2$NHR$^4$, in which $R^4$ is as defined above, takes place to form (Ia) and (Ib).

Preferred is a process according to the invention, where the radicals in formula (Ia), (Ib), (II), (III), (IV) and (V) are defined as follows:
$R^1$ and $R^3$ are each independently selected from difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-difluoroethyl, 2,2-dichloro-2-fluoroethyl, 2,2,2-trichloroethyl, tetrafluoroethyl (CF$_3$CFH), pentafluoroethyl and 1,1,1-trifluoroprop-2-yl;
$R^2$ is selected from H, F, Cl, Br, COOCH$_3$, COOC$_2$H$_5$, COOC$_3$H$_7$, CN and CON(CH$_3$)$_2$, CON(C$_2$H$_5$)$_2$;

$R^4$ is selected from H, $C_1$-$C_5$ alkyl, aryl, pyridyl;

$R^8$ are each independently selected from methyl, ethyl, n-, iso-propyl, n-, iso-, sec-und t-butyl, cyclopropyl, cyclobutyl, cyclopentyl, cyclohexyl, phenyl, benzyl, phenylethyl, tolyl, 2,3-, 2,4-, 2,5-, 2,6-, 3,4- or 3,5-dimethylphenyl;

X is selected from F, Cl or —O(CO)$R^1$.

More preferred is a process according to the invention, where the radicals in formula (Ia), (Ib), (II), (III), (IV) and (V) are defined as follows:

$R^1$ and $R^3$ are each independently selected from trifluoromethyl, difluoromethyl, difluorochloromethyl, pentafluoroethyl;

$R^2$ is selected from H, Cl, CN, COO($C_2H_5$)$_2$;

$R^4$ is selected from H, methyl, ethyl, n-, isopropyl, n-, iso-, sec- and t-butyl, n-pentyl, n-hexyl, 1,3-dimethylbutyl, 3,3-dimethylbutyl, aryl;

$R^8$ is selected from methyl, ethyl, n-, iso-propyl, n-, iso-, sec-und t-butyl, cyclopropyl, cyclobutyl, cyclopentyl, cyclohexyl, benzyl;

X is selected from F, Cl or —OC(O)$R^1$.

Even more preferred is a process according to the invention, where the radicals in formula (Ia), (Ib), (II), (III), (IV) and (V) are defined as follows:

$R^1$ and $R^3$ are each independently selected from $CF_2H$, $CF_3$;

$R^2$ is selected from H or $COOC_2H_5$;

$R^4$ is selected form H, methyl, ethyl, phenyl;

$R^8$ is selected from ethyl, n-, iso-propyl, n-, cyclopentyl, cyclohexyl, benzyl;

X is Cl or F.

Most preferred is a process according to the invention, where the radicals in formula (Ia), (Ib), (II), (III), (IV) and (V) are defined as follows:

$R^1$ and $R^3$ are each independently selected from $CF_2H$, $CF_3$;

$R^2$ is H;

$R^4$ is selected from H, methyl, phenyl;

$R^8$ is selected from iso-propyl, benzyl;

X is Cl or F.

Surprisingly, the pyrazoles of the formula (I) can be prepared under the inventive conditions with good yields and in high purity, which means that the process according to the invention overcomes the abovementioned disadvantages of the preparation processes previously described in the prior art.

General Definitions

In the context of the present invention, the term "halogen" (Hal), unless defined differently, comprises those elements which are selected from the group comprising fluorine, chlorine, bromine and iodine, preferably fluorine, chlorine and bromine, more preferably fluorine and chlorine.

Optionally substituted groups may be mono- or polysubstituted, where the substituents in the case of polysubstitutions may be the same or different.

Haloalkyl: straight-chain or branched alkyl groups having 1 to 6 and preferably 1 to 3 carbon atoms (as specified above), where some or all of the hydrogen atoms in these groups may be replaced by halogen atoms as specified above, for example (but not limited to) $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloro ethyl, 1-bromoethyl, 1-fluoroethyl, 2-fluoroethyl, 2,2-difluoroethyl, 2,2,2-trifluoroethyl, 2-chloro-2-fluoroethyl, 2-chloro, 2-difluoroethyl, 2,2-dichloro-2-fluoroethyl, 2,2,2-trichloroethyl, pentafluoroethyl and 1,1,1-trifluoroprop-2-yl. This definition also applies to haloalkyl as part of a composite substituent, for example haloalkylaminoalkyl etc., unless defined elsewhere. Preference is given to alkyl groups substituted by one or more halogen atoms, for example trifluoromethyl ($CF_3$), difluoromethyl ($CHF_2$), $CF_3CH_2$, $CF_2Cl$ or $CF_3CCl_2$.

Alkyl groups in the context of the present invention, unless defined differently, are linear or branched saturated hydrocarbyl groups. The definition $C_1$-$C_{12}$-alkyl encompasses the widest range defined herein for an alkyl group. Specifically, this definition encompasses, for example, the meanings of methyl, ethyl, n-, isopropyl, n-, iso-, sec- and t-butyl, n-pentyl, n-hexyl, 1,3-dimethylbutyl, 3,3-dimethylbutyl, n-heptyl, n-nonyl, n-decyl, n-undecyl or n-dodecyl.

Cycloalkyl: monocyclic, saturated hydrocarbyl groups having 3 to 8 and preferably 3 to 6 carbon ring members, for example (but not limited to) cyclopropyl, cyclopentyl and cyclohexyl. This definition also applies to cycloalkyl as part of a composite substituent, for example cycloalkylalkyl etc., unless defined elsewhere.

Aryl groups in the context of the present invention, unless defined differently, are aromatic hydrocarbyl groups which may have one, two or more heteroatoms selected from O, N, P and S. The definition $C_{6-18}$-aryl encompasses the widest range defined herein for an aryl group having 5 to 18 skeleton atoms, where the carbon atoms may be exchanged for heteroatoms. Specifically, this definition encompasses, for example, the meanings of phenyl, cycloheptatrienyl, cyclooctatetraenyl, naphthyl and anthracenyl; 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; 1-pyrrolyl, 1-pyrazolyl, 1,2,4-triazol-1-yl, 1-imidazolyl, 1,2,3-triazol-1-yl, 1,3,4-triazol-1-yl; 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Arylalkyl groups (aralkyl groups) in the context of the present invention, unless defined differently, are alkyl groups which are substituted by aryl groups, may have one $C_{1-8}$-alkylene chain and may have, in the aryl skeleton, one or more heteroatoms selected from O, N, P and S. The definition $C_{7-19}$-aralkyl group encompasses the widest range defined herein for an arylalkyl group having a total of 7 to 19 atoms in the skeleton and alkylene chain. Specifically, this definition encompasses, for example, the meanings of benzyl and phenylethyl.

Alkylaryl groups (alkaryl groups) in the context of the present invention, unless defined differently, are aryl groups which are substituted by alkyl groups, may have one $C_{1-8}$-alkylene chain and may have, in the aryl skeleton, one or more heteroatoms selected from O, N, P and S. The definition $C_{7-19}$-alkylaryl group encompasses the widest range defined herein for an alkylaryl group having a total of 7 to 19 atoms in the skeleton and alkylene chain. Specifically, this definition encompasses, for example, the meanings of tolyl or 2,3-, 2,4-, 2,5-, 2,6-, 3,4- or 3,5-dimethylphenyl.

The term intermediate used in the context of the present invention describes the substances which occur in the process according to the invention and are prepared for further chemical processing and are consumed or used therein in order to be converted to another substance. The intermediates can often be isolated and intermediately stored or are used without prior isolation in the subsequent reaction step. The term "intermediate" also encompasses the generally unstable and short-lived intermediates which occur transiently in multistage reactions (staged reactions) and to which local minima in the energy profile of the reaction can be assigned.

The inventive compounds may be present as mixtures of any different isomeric forms possible, especially of stereoisomers, for example E and Z isomers, threo and erythro isomers, and optical isomers, but if appropriate also of tautomers. Both the E and the Z isomers are disclosed and claimed, as are the threo and erythro isomers, and also the optical isomers, any mixtures of these isomers, and also the possible tautomeric forms.

Process Description

The process is illustrated in Scheme 1:

Scheme 1:

Step A:

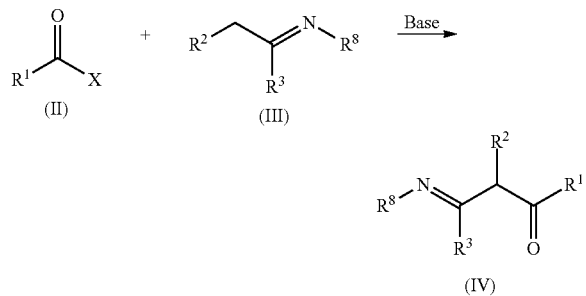

Step B:

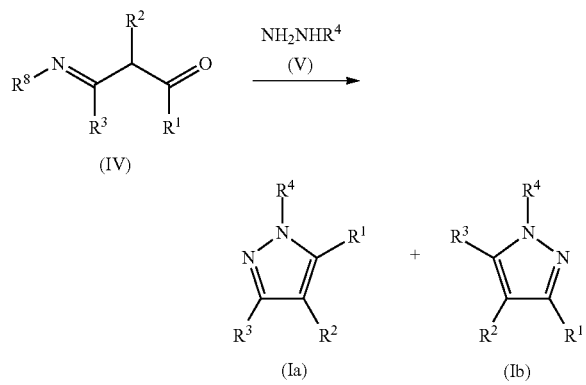

Step A:

In step A acid derivatives of the formula (II) are reacted, in the presence of a base, with compounds of the formula (III).

Preferred compounds of the general formula (II) are Trifluoracetylchloride, Trifluoracetylfluoride, Difluoracetylfluoride, Difluoroacetylchloride, Trifluorocetylbromide. It is also possible to generate compounds of formula (II) in situ for instance using trifluoroacetic acid, pivaloyl chloride and pyridine (see WO 2003/051820).

The synthesis of compounds of the formula (IV) according to the invention is effected at temperatures of 0° C. to +120° C., preferably at temperatures of +20° C. to +100° C., more preferably at 20° C. to +60° C. and under standard pressure. Typical bases are: trialkylamines, pyridine, alkylpyridines, picolines, DBU. Preferred is pyridine as a base.

The reaction time is not critical and may, according to the batch size and temperature, be selected within a range between a few minutes and several hours.

For step A 1 to 2 mol, preferably 1 to 1.5 mol, most preferably 1 to 1.2 mol of the acid derivative of the formula (II) is reacted with 1 mol of compound of the formula (III).

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane. Particular preference is given, for example, to THF, acetonitriles, ethers, toluene, xylene, chlorobenzene, n-hexane, cyclohexane or methylcyclohexane, and very particular preference, for example, Dichloromethane, ether or dichloromethane. Compounds of the formula (IV) can be used in the cyclization step without prior workup. Alternatively, they can be isolated by suitable workup steps, characterized and optionally further purified.

Compounds of the formula (III) can be prepared from aldehydes or ketones and primary amines. The preparation is effected at temperatures between 10 and 110° C., usually without any solvents, or in organic solvents like toluene, dichloromethame or ethers. Lewis acid like $BF_3$, $TiCl_4$ could be also used to accelerate the formation of ketimines (see also Röschentahller et al, J. Fluorine. Chem. v. 125, n. 6, 1039-1049 and Tetrahedron, 69 (2013), 3878-3884).

Step B:

Step B is the cyclization reaction of compounds of the formula (IV) in the presence of compounds of the formula (V).

In step B 1 mol to 2 mol, preferably 1 to 1.5 mol of the hydrazine of the formula (V) for 1 mol of the compound of formula (IV) is used.

The cyclization in step B is effected at temperatures of −40° C. to +80° C., preferably at temperatures of +20° C. to +70° C., more preferably at +60° C. and under standard pressure.

The reaction time is not critical and may, according to the batch size, be selected within a relatively wide range.

Typically, the cyclization step B is effected without changing the solvent.

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane, alcohols such as methanol, ethanol, isopropanolm butanol. Particular preference is given, for example, to THF, acetonitriles, ethers, toluene, xylene, chlorobenzene, n-hexane, cyclohexane or methylcyclohexane, ethanol and very particular preference, for example, to acetonitrile, THF, ether, dichloromethane, ethanol.

Typically, the cyclization of compounds of the formula (IV) and (V) proceeds under acidic condition.

Preference is given to mineral acids, for example $H_2SO_4$, HCl, HF, HBr, HI, $H_3PO_4$ or organic acids, for example CH3COOH, $CF_3COOH$, p-toluenesulphonic acid, methanesulphonic acid, trifluoromethanesulphonic acid. 0.1 mol to 2 mol, preferably 0.1 to 1.5 mol of the acid for 1 mol of the compound of formula (IV) is used.

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; alcohols such as methanol, ethanol, isopropanol or butanol, nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane. Particular preference is given, for example, to acetonitrilestoluene, xylene, chlorobenzene, n-hexane, cyclohexane or methylcyclohexane, and very particular preference, for example, to acetonitriles, THF, toluene or xylene. After the reaction has ended, for example, the solvents are removed and the product is isolated by filtration, or the product is first washed with water and extracted, the organic phase is removed and the solvent is removed under reduced pressure.

The compounds of the formula (Ia) and (Ib) where $R^2$ equals $(CO)OR^5$ can then be converted to pyrazole acids of the formula (I) where $R^2$ equals COOH.

Amine (IV) can be reused for the preparation of compound (III). Alternatively, it is trapped by washing the reaction mixture with acid.

The invention is illustrated by the following examples:

EXAMPLE 1

N-(1,1-difluoropropan-2-ylidene)propan-2-amine, (III-1)

To the mixture of difluoracetone (94 g, 1 mol) in 500 ml methyltert-butylether (88 g., 1.5 mol) of isopropylamin was added at 10° C. After 1 h (70 g 0.5 mol) of $BF_3*Et_2O$ was added and the mixture was stirred additionally for 1 h. Organic solution was separated from bottom syrup and solvent was distilled off at atmospheric pressure. The remaining liquid was distilled in vacuum yielding 139 g ketimine with a of b.p. 70-72° C./400 mbar.

$^1$H NMR (400 MHz, $CDCl_3$): ☐☐ 5, 9 (t, 1H), 3,7 (m, 1H), 1, 8 (s, 3H), 1, 1 (d, 6H) ppm.

$^{19}$F (376 MHz, $CDCl_3$) ☐☐☐☐–122 (d, 2F) ppm.

EXAMPLE 2

N-1,1-difluoropropan-2-ylidene-1-phenylmethanamine, (III-2)

To the mixture of difluoroacetone (94 g, 1 mol) in 500 ml Toluene, (107 g, 1 mol) of benzylamine was slowly added at 10° C. After 6 h at 20° C. toluene$_2$ was distilled off at reduced pressure and the remains liquid was used without purification 170 g.

$^1$H NMR (400 MHz, $CDCl_3$) ☐☐ 7, 2-7, 4 (m, 5H), 5, 9 (t, 1H), 4, 5 (s, 2H), 2, 0 (s, 3H) ppm.

$^{19}$F (376 MHz, $CDCl_3$) ☐☐☐–1118 (d, 2F) ppm.

EXAMPLE 3

N-(1,1,1-trifluoropropan-2-ylidene)propan-2-amine, (III-3)

Preparation see Example 2, b.p. 80-82° C.

EXAMPLE 4

N-1,1,1-trifluoropropan-2-ylidene-1-phenylmethanamin (III-4)

Preparation see Example 2, b.p. 90-91° C., 1.5 mbar.

EXAMPLE 5

3,5-bis(difluoromethyl)pyrazole, (I-1)

A solution of 10.4 (75 mmol) of N-(1,1-difluoropropan-2-ylidene)propan-2-amine and 12 g Pyridine in 100 ml of Dichloromethane was cooled to 0° C. 19.5 g of Difluoroacetic acid anhydride was added portionwise at this temperature e under intensive stirring and the mixture was finally stirred at 10° C. for 6 h. 50 ml HCl (as 5% water solution) and 20 g hydrazinhydrate were added slowly to the reaction solution to keep the temperature under 40° C. and the mixture was stirred for 5 h at 40° C. 100 ml water and 100 ml Dichloromethane were added and organic layer was separated, washed with water, dried over $MgSO_4$ and concentrated in vacuum to give an oily product. Vacuum distillation at 92-95° C./1 mbar gave 8.8 g (70%) of pure 3,5-bis(difluoromethyl)-1H-pyrazole b) as a white solid with a of m.p. 70-71° C.

$^1$H NMR (400 MHz, $CDCl_3$) ☐ 12.5 (br, 1H), 6.77 (t, 2H, J=54.8 Hz), 6.74 (s, 1H) ppm.

EXAMPLE 6

3-(difluoromethyl)-5-(trifluoromethyl)-1H-pyrazole, (I-2)

Similar obtained from N-(1,1-difluoropropan-2-ylidene) propan-2-amine and trifluoroacetic acid anhydride.

Yield 78%.

$^1$H NMR (400 MHz, $CDCl_3$) ☐ 12.6 (br, 1H), 6.81 (s, 1H), 6.76 (t, 1H, J=54.5 Hz); $^{13}$C (101 MHz, $CDCl_3$) ☐☐ 140.7, 128.8, 120.3 (q, $J_{C-F}$=266 Hz), 108.5 (t, $J_{C-F}$=237 Hz), 103.8; $^{19}$F (376 MHz, $CDCl_3$) ☐☐–61.7 (s, 3F), –112.9 (d, 2F, J=54.7 Hz); HRMS (ESI) calculated for $C_5H_4F_5N_2$ $[M+H]^+$ 187.029, found 187.029.

The invention claimed is:

1. A process for preparing a compound of the formula (Ia) or a compound of the formula (Ib),

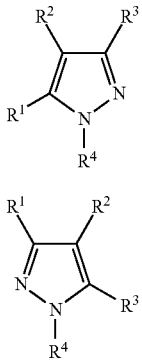

in which
R$^1$ and R$^3$ are each independently C$_1$-C$_6$-haloalkyl;
R$^2$ is selected from the group consisting of H, halogen, COOH, (C=O)OR$^5$, CN, and (C=O)NR$^6$R$^7$;
R$^4$ is selected from the group consisting of H, C$_1$-C$_8$ alkyl, aryl, and pyridyl;
R$^5$ is selected from the group consisting of C$_{1-12}$-alkyl, C$_{3-8}$-cycloalkyl, C$_{6-18}$-aryl, C$_{7-19}$-arylalkyl, and C$_{7-19}$-alkylaryl;
R$^6$ and R$^7$ are each independently selected from the group consisting of C$_{1-12}$-alkyl, C$_{3-8}$-cycloalkyl, C$_{6-18}$-aryl, C$_{7-19}$-arylalkyl, and C$_{7-19}$-alkylaryl, or where
R$^6$ and R$^7$ together with the nitrogen atom to which they are bonded form a four-, five-, or six-membered ring;
characterized in that a compound of the formula (II),

in which
R$^1$ is as defined above;
X is F, Cl, Br, or —OC(O)R$^1$;
is reacted with a compound of the formula (III),

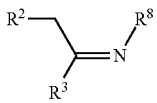

in which
R$^8$ is selected from the group consisting of C$_{1-12}$-alkyl, C$_{3-8}$-cycloalkyl, C$_{6-18}$-aryl, C$_{7-19}$-arylalkyl, C$_{7-19}$-alkylaryl, and OR$^9$;
R$^9$ is selected from the group consisting of C$_{1-12}$-alkyl, C$_{3-8}$-cycloalkyl, C$_{6-18}$-aryl, C$_{7-19}$-arylalkyl, and C$_{7-19}$-alkylaryl;
R$^2$ and R$^3$ are as defined above;

to form a compound of formula (IV)

in which
R$^1$, R$^2$, R$^3$, R$^5$, R$^6$, R$^7$, R$^8$, and R$^9$ are as defined above; and characterized in that the compound of the formula (IV) is reacted with a compound of the formula (V)

NH$_2$NHR$^4$  (V)

in which R$^4$ is as defined above;
to form the compound of the formula (Ia) or the compound of the formula (Ib).

2. The process according to claim 1, characterized in that
R$^1$ and R$^3$ are each independently selected from the group consisting of difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-difluoroethyl, 2,2-dichloro-2-fluoroethyl, 2,2,2-trichloroethyl, tetrafluoroethyl (CF$_3$CFH), pentafluoroethyh and 1,1,1-trifluoroprop-2-yl;
R$^2$ is selected from the group consisting of H, F, Cl, Br, COOCH$_3$, COOC$_2$H$_5$, COOC$_3$H$_7$, CN, CON(CH$_3$)$_2$, and CON(C$_2$H$_5$)$_2$;
R$^4$ is selected from the group consisting of H, C$_1$-C$_8$ alkyl, aryl, and pyridyl;
R$^8$ is selected from the group consisting of methyl, ethyl, n-propyl, iso-propyl, n-butyl, iso-butyl, sec-butyl, t-butyl, cyclopropyl, cyclobutyl, cyclopentyl, cyclohexyl, phenyl, benzyl, phenylethyl, tolyl, 2,3-dimethylphenyl, 2,4-dimethylphenyl, 2,5-dimethylphenyl, 2,6-dimethylphenyl, 3,4-dimethylphenyl, and 3,5-dimethylphenyl; and
X is selected from F, Cl or —O(CO)R$^1$.

3. The process according to claim 1, characterized in that
R$^1$ and R$^3$ are each independently selected from the group consisting of trifluoromethyl, difluoromethyl, difluorochloromethyl, and pentafluoroethyl;
R$^2$ is selected from the group consisting of H, Cl, CN, and COO(C$_2$H$_5$)$_2$;
R$^4$ is selected from the group consisting of H, methyl, ethyl, n-propyl, iso-propyl, n-butyl, iso-butyl, sec-butyl, t-butyl, n-pentyl, n-hexyl, 1,3-dimethylbutyl, 3,3-dimethylbutyl, and aryl;
R$^8$ is selected from the group consisting of methyl, ethyl, n-propyl, iso-propyl, n-butyl, iso-butyl, sec-butyl, t-butyl, cyclopropyl, cyclobutyl, cyclopentyl, cyclohexyl, and benzyl; and
X is selected from the group consisting of F, Cl and —OC(O)R$^1$.

4. The process according to claim 1, characterized in that
R$^1$ and R$^3$ are each independently selected from the group consisting of CF$_2$H and CF$_3$;
R$^2$ is selected from the group consisting of H and COOC$_2$H$_5$;
R$^4$ is selected from the group consisting of H, methyl, ethyl, and phenyl;

$R^8$ is selected from the group consisting of ethyl, n-propyl, iso-propyl, n-, cyclopentyl, cyclohexyl, and benzyl; and X is Cl or F.

5. The process according to claim 1, characterized in that $R^1$ and $R^3$ are each independently selected from the group consisting of $CF_2H$ and $CF_3$;

$R^2$ is H;

$R^4$ is selected from the group consisting of H, methyl, and phenyl;

$R^8$ is selected from the group consisting of iso-propyl and benzyl; and

X is Cl or F.

\* \* \* \* \*